United States Patent
Moser et al.

(10) Patent No.: US 10,073,019 B2
(45) Date of Patent: Sep. 11, 2018

(54) RAPID QUANTITATIVE ELEMENT TESTING

(71) Applicant: CEM Corporation, Matthews, NC (US)

(72) Inventors: Cindy Moser, Monroe, NC (US); Michael Collins, Sr., Matthews, NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 14/931,263

(22) Filed: Nov. 3, 2015

(65) Prior Publication Data

US 2016/0131561 A1   May 12, 2016

Related U.S. Application Data

(60) Provisional application No. 62/080,449, filed on Nov. 17, 2014, provisional application No. 62/076,025, filed on Nov. 6, 2014.

(51) Int. Cl.
| | |
|---|---|
| *G01N 1/44* | (2006.01) |
| *G01N 33/02* | (2006.01) |
| *G01N 21/31* | (2006.01) |
| *G01N 21/72* | (2006.01) |
| *G01N 21/73* | (2006.01) |

(52) U.S. Cl.
CPC .............. *G01N 1/44* (2013.01); *G01N 33/02* (2013.01); *G01N 21/3103* (2013.01); *G01N 21/72* (2013.01); *G01N 21/73* (2013.01)

(58) Field of Classification Search
CPC ..................................................... G01N 33/02
See application file for complete search history.

(56) References Cited

U.S. PATENT DOCUMENTS

| | | | |
|---|---|---|---|
| 3,015,983 A | 1/1962 | Staunton | |
| 3,088,808 A | 5/1963 | Mandell, Jr. | |
| 3,938,888 A | 2/1976 | Folsom | |
| 4,097,239 A | 6/1978 | Patterson | |
| 4,133,996 A * | 1/1979 | Fread ...................... | A47J 29/00 |
| | | | 219/729 |
| 4,234,257 A | 11/1980 | Carter | |
| 4,303,615 A | 12/1981 | Jarmell | |

(Continued)

FOREIGN PATENT DOCUMENTS

| | | |
|---|---|---|
| CA | 1063829 | 10/1979 |
| CA | 2853577 | 12/2014 |

(Continued)

OTHER PUBLICATIONS

Carr et al. "The use of microwave technology for dry ashing procedures", Mar. 1991.*

(Continued)

*Primary Examiner* — Paul S Hyun
(74) *Attorney, Agent, or Firm* — Parsons Summa

(57) ABSTRACT

A method of element testing is disclosed that includes the steps of weighing a sample, pressing the sample between pads, applying microwave radiation to the sample and pads in the presence of a microwave susceptor material and ashing the pressed sample, adding the pads and the ashed sample to an acid, and forwarding filtrate from the pad-sample-acid mixture to a spectrometer.

10 Claims, 9 Drawing Sheets

(56) References Cited

U.S. PATENT DOCUMENTS

| | | | |
|---|---|---|---|
| 4,565,669 | A | 1/1986 | Collins |
| 4,845,053 | A | 7/1989 | Zajac |
| 4,896,965 | A | 1/1990 | Goff |
| 5,318,754 | A | 6/1994 | Collins |
| 5,492,832 | A | 2/1996 | Shirazi |
| 2014/0320858 | A1 | 10/2014 | Goldring |

FOREIGN PATENT DOCUMENTS

| | | |
|---|---|---|
| CN | 201007698 | 1/2008 |
| CN | 101430262 | 5/2009 |
| CN | 201607277 | 10/2010 |
| CN | 102116767 | 7/2011 |
| CN | 102937587 | 2/2013 |
| CN | 103412034 | 11/2013 |
| CN | 103424306 | 12/2013 |
| CN | 103534587 | 1/2014 |
| CN | 103558167 | 2/2014 |
| DE | 102004020350 | 11/2005 |
| EP | 0717250 | 11/2000 |
| GB | 1071123 | 7/1967 |
| JP | 2006284240 | 10/2006 |

OTHER PUBLICATIONS

Mutalik et al. "Determination of estimation of potassium ion in dry fruits by flame photometry and their proximate analysis", 2011, Journal of Chemical and Pharmaceutical Research 3(6), pp. 1097-1102.*

Sapp et al., Microwave Digestion of Multi-Component Foods for Sodium Analysis by Atomic Absorption Spectrometry, Journal of Food Science, vol. 56, No. 5, 1991, 3 pgs.

Friel et al., Dry- and Wet-Ashing Techniques Compared in Analyses for Zinc, Copper, Manganese, and Iron in Hair, Clinical Chemistry, vol. 32, No. 5, 1986, pp. 739-742.

Theory of Sample Preparation Using Acid Digestion, Pressure Digestion and Microwave Digestion (Microwave Decomposition); Berghof Products + Instruments GmbH; [Date Unknown] 11 pgs.

Gelski, Jeff; Kraft v.p.: Measure Sodium to Reduce it effectively; Food Business News, Mar. 21, 2014; 1 pg.

Burck H.C. ( English translation of Section 1. Ashing Method); Veraschungsschnellmethode zur flammenphotometrischen Bestimmung von Gewebsnatrium and -kalium; 1961; 6 pgs.

"Determination of Sodium and Calcium by ICP Atomic Emission Spectroscopy"; US Department of Agriculture Food Safey and Inspection Service, Office of Public Health Service; Sep. 25, 2014; pp. 1-10.

Welna et al., Quality of the Trace Element Analysis: Sample Preparation Steps, Wide Spectra of Quality Control, 2011, pp. 53-70.

Testing for Sodium and Calcium; MeatPoultry.com; Oct. 7, 2014; 1 pg.

A Guide to Single Channel Flame Photometer Analysis; Sherwood Scientific LTD, [date unknown]; 45 pgs.

Bergman, Theodore L., et al. Fundamentals of Heat and Mass Transfer, 8th Edition. Wiley, 2017. Kindle edition; 6 pgs.

* cited by examiner

RAPID QUANTITATIVE ELEMENT TESTING

BACKGROUND

The present invention relates to rapid testing for elemental materials and in particular relates to rapid testing for Group I and Group II elements in food products.

The composition of food products is a topic of significant interest on several levels, particularly when the food is prepared or prepackaged; e.g., canned, frozen, refrigerated, or otherwise provided to the consumer in a modern food supply chain environment. In addition to consumer preferences such as taste, appearance, and price; legal regulations in the United States (and similar regulations elsewhere in the world) require the packaged food be labeled with accurate information about its contents.

Frequent candidates for compositional analysis include fats and oils, proteins, carbohydrates, synthetic additives, and trace elements. Sodium, typically present as sodium chloride (NaCl; "salt") is of particular interest. In addition to its usual recognition as enhancing the taste of food, sodium is a necessary element for sustaining life and good health, and is a well-known preservative for many foods. Sodium is also present, however, as sodium bicarbonate in other common food agents such as baking powder and baking soda The skilled person recognizes that although the word "salt" is widely used to refer to sodium chloride, the term has a more precise meaning in a formal chemistry sense and covers any compound that is generally formed of alternating positive and negative ions, usually in an ordered crystal structure.

Nevertheless, an excess of dietary sodium has been linked (directly or indirectly) to undesired health consequences such as hypertension ("high blood pressure"), heart attacks, stroke, heart failure, and other cardiovascular disease. Other potential (although more tenuous) problems may include higher risks for osteoporosis or cancer.

In some prepared foods, sodium is not naturally present, and thus can be added carefully in desired measured amounts. In other foods, however, the amount of sodium can vary widely (relatively speaking) and be less predictable to the packager or the consumer on a case-by-case or item-by-item basis. As examples, higher amounts of salt are often present in cheese, processed meats, snack foods, and canned soup.

Alternatively, because salt is a preservative, reducing the total amount of sodium in a given food product will change—and typically shorten—the shelf life of that product. The potassium ion ($K^{+1}$) can replace the sodium ion ($Na^{+1}$) for some purposes, but has different taste qualities than sodium and thus cannot simply replace sodium in the absence of some other adjustment or result.

Nevertheless, because potassium chloride (KCl) is replacing some or all of the sodium chloride in a number of food products, the presence and amount of potassium represents valuable information.

Calcium content is also important in a number of food products and is particularly important in dairy products because it affects several relevant properties, and particularly affects the properties of cheese. Calcium is important in the rendering aspect of the poultry industry, because the measurement of calcium is generally used as the most accurate method of determining the bone content in (for example) animal feed meal made from poultry products.

Lithium content is important in both medical and industrial applications. Barium has no known health benefits (the human body contains about 0.00003%) and instead represents a health risk if present in more than trace amounts The effort to raise, lower, or maintain an appropriate level of an element such as sodium in a food product thus requires testing. Conventional sodium testing, however, presents disadvantages, and in some cases problems, in the food preparation and packaging context.

For example, the Food Safety and Inspection Service (FSIS) of the U.S. Department of agriculture (USDA) recently approved a sodium test that includes at least about 4 hours of ramp time and 15 hours of dwell time (CLG-SOCAL3.00; "Determination of Sodium and Calcium by ICP Atomic Emission Spectroscopy;" Sep. 25, 2014).

In the preparation of large quantities of packaged or prepared foods, longer testing times raise several disadvantages or problems. First, fewer tests can be carried out over any given time interval, thus reducing the amount of data produced and available. Second if the packaging or production steps are carried out on a continuous or near-continuous basis, the time interval needed for testing requires that (1) production be halted until an answer is determined, or (2) if production continues while testing is carried out, the testing interval creates a risk that a large proportion of undesired product will be made during the testing interval Sodium is traditionally tested (quantitatively measured) by titrating with a silver nitrate ($AgNO_3$) solution of known concentration that will react with the chloride ion ($Cl^{-1}$) in sodium chloride to produce a solid precipitate, and potentially with a potassium chromate solution ($K_2CrO_4$) to add a color change at the endpoint of the silver chloride reaction.

Although titration is rapid, it is actually a test for chloride ion ($Cl^{-1}$) content based upon the assumption that the chloride ion is entirely present as sodium chloride (NaCl). Thus, if all of the chloride is indeed present as sodium chloride the test is accurate, but when another salt is the chloride ion source, the assumption breaks down and the test results for sodium are inaccurate. Stated differently, the titration test cannot distinguish between or among sodium chloride, potassium chloride, or lithium chloride.

Sodium in food can also be determined by now-conventional microwave digestion in acid. Although microwave digestion techniques offer advantages (for example the use of acids at temperatures above their boiling point in sealed vessels), and although microwave heating is generally much faster than conventional conductive or convection heating, the steps required for sample preparation, digestion, filtration, dilution and analysis, nevertheless can take up to an hour for each sample. In particular, acid digestion is a relatively slow process even with microwave energy because the steps of ramping the temperature, holding the temperature, and cooling thereafter, are required regardless of the speed of the heating step. The concentrated acids used in acid digestion are also disadvantageous, or inappropriate, or simply too complex to be conveniently handled in a normal plant environment.

Sodium content testing can also be carried out by dry ashing using microwave techniques, but in some cases the ashing step must be carried out for as long as 12-24 hours; i.e., an interval far too inconvenient for rapid food testing purposes.

Carrying out digestion techniques at even higher temperatures can increase speeds, but can also reduce the amount of recovered element in a form that can be tested, thus sacrificing accuracy. Furthermore, the longer a sample is heated, and the higher the temperature to which it is heated, the longer the time required before the sample can be handled for solution and spectroscopy purposes.

A number of elements begin to volatilize as temperatures approach or exceed 500° C. and in a testing protocol that seeks to capture an element, such a volatile loss produces inaccurate results.

Faster (more rapid) tests are available, but also present specific disadvantages. A recent option is X-ray fluorescence. As a brief explanation of the technique, high energy x-rays or gamma rays are used to displace electrons from inner orbitals of elemental atoms in a sample. When another electron drops into the empty orbital from a higher energy orbital, the transition generates a fluorescent photon with a characteristic energy. The detection and analysis of these fluorescent photons provide a quantitative measurement of the amount of the element in the original sample.

Although accurate and powerful, X-ray fluorescence presents disadvantages in the food testing context. The method is sensitive to the matrix in which the element is found, generates heat, requires sophisticated sample preparation, generally requires a state or Federal license, and uses large and expensive instruments. In particular, the X-ray fluorescence test must be adjusted or customized for almost every different food product being tested; i.e., hundreds of protocols are required.

Therefore, a need remains for a less expensive, less complex, and (perhaps most importantly) more rapid technique for accurately determining the proportional quantity of elements—particularly sodium—in compositions, and particularly food compositions.

SUMMARY

In one aspect the invention is a method of preparing a food sample for quantitative sodium testing that includes the steps of pressing a weighed sample between pads that are microwave transparent, porous, absorbent, have low thermal mass, have high decomposition temperatures, and do not contain sodium; and then applying microwave radiation to the sample and pads in the presence of a microwave susceptor material until the pressed sample ashes.

In another aspect, the invention is a method of element testing that includes the steps of weighing a sample, pressing the sample between pads, applying microwave radiation to the sample and pads in the presence of a microwave susceptor material until the pressed sample ashes, adding the pads and the sample to an acid, and forwarding filtrate from the pad-sample-acid mixture to a spectrometer.

In yet another aspect the invention is a sample for elemental testing that includes a pressed layer of a food product between two layers of a material that is porous, absorbent, has low thermal mass, is microwave transparent, has high decomposition temperature, and does not contain the element being tested.

The foregoing and other objects and advantages of the invention and the manner in which the same are accomplished will become clearer based on the followed detailed description taken in conjunction with the accompanying drawings.

DETAILED DESCRIPTION

The invention is a dry ashing technique that permits rapid sample oxidation followed by acid dilution and flame photometry of intended elements, and sodium in particular. In most circumstances the entire test can be carried out in 10 minutes or less. By comparison, conventional ashing takes 12-24 hours, and even microwave ashing for a standard sample (4 grams) can take overnight.

Although the invention is described herein in terms of sodium content in a food product, the rapid test of the invention is appropriate for evaluating sodium, potassium, lithium, barium and calcium in other types of compositions such as (but not limited to) petroleum products, soil, and cosmetics.

Sodium, potassium, lithium, barium and calcium are all detectable at relatively low temperatures in a flame photometer; e.g., a propane flame in air reaches temperatures sufficient to identify these elements. This eliminates the need for gases that produce higher temperature flames, but which are more expensive, more difficult to handle, or both (e.g., acetylene and acetylene mixtures).

Figure 1:
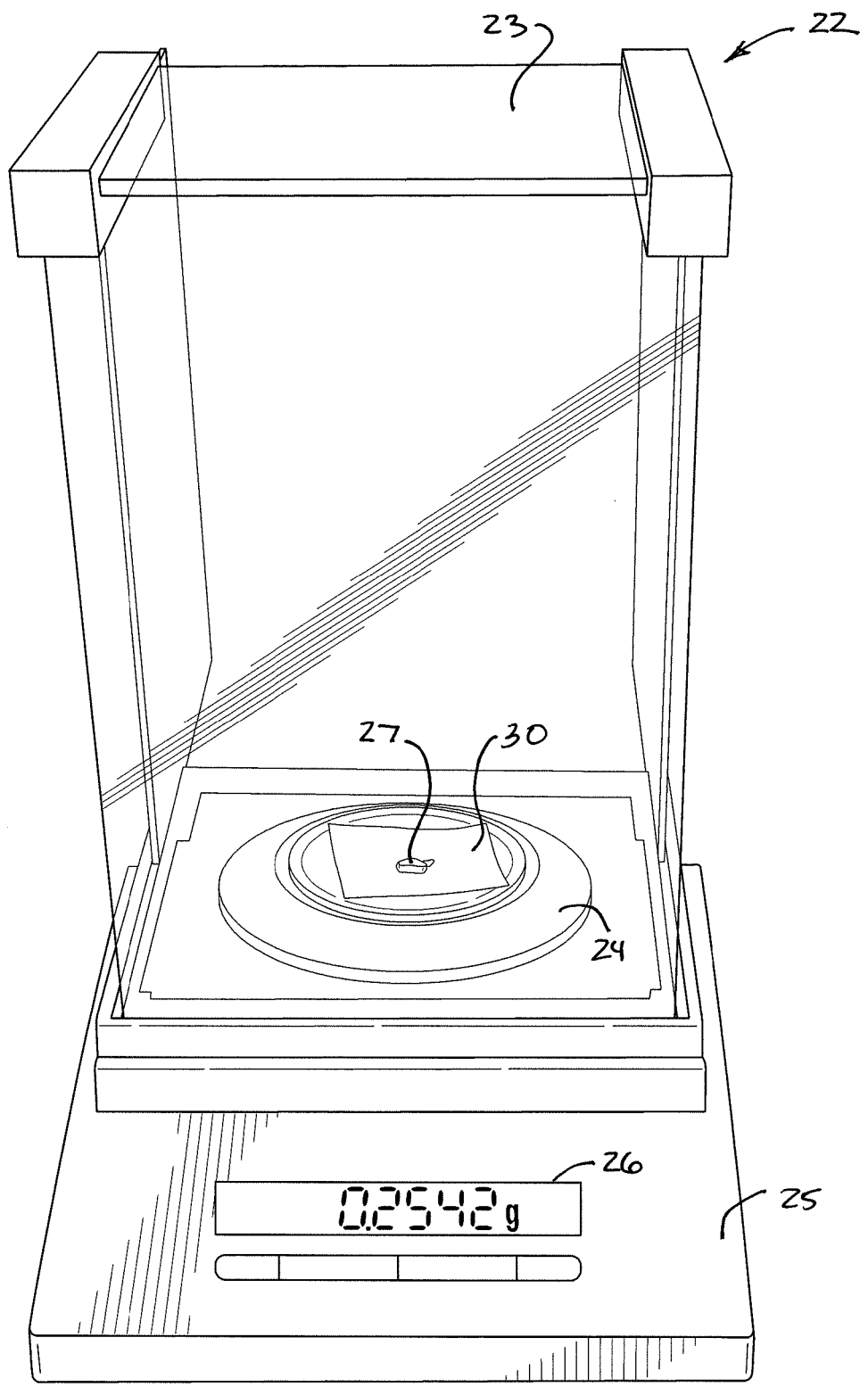
FIG. 1 is a perspective view of an analytical balance used in the method of the invention.

FIG. 1 is a perspective view of a precision balance broadly designated at 22. Balances of this type are well understood in the art and will not be otherwise described in detail, with Mettler-Toledo Inc., Columbus, Ohio 43240 being one leading manufacturer.

Because of the small sample sizes used in the method and the desirability of a high level of precision and accuracy, the balance is preferably surrounded by a balance enclosure 23. In many cases the enclosure is formed of transparent material (glass, polycarbonate, etc.) and prevents small air currents from creating lift (and thus weighing errors) on the balance pan 24.

The weighing mechanism is generally inside of a balance housing 25 which includes a digital display 26 which typically incorporates liquid crystals or light emitting diodes to give a precise readout of the sample weight.

FIG. 1 further illustrates a raw (i.e., untreated) sample 27 such as cheese on a sample pad 30. After the weight of the sample pad is tared, the weight of the pad and sample are recorded for further use.

Figure 2:
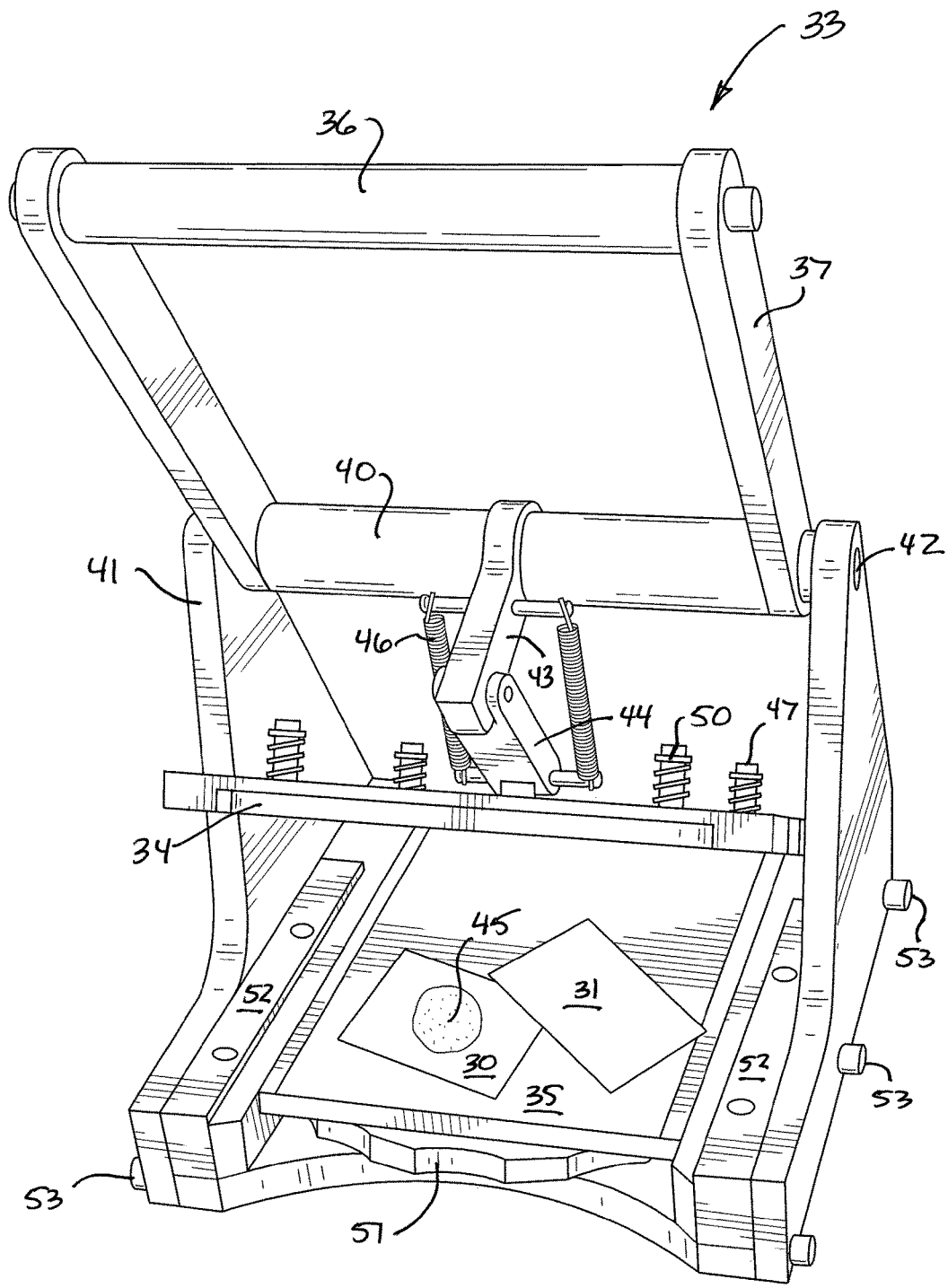
FIG. 2 is a perspective view of the sample press according to the invention.
Figure 3:
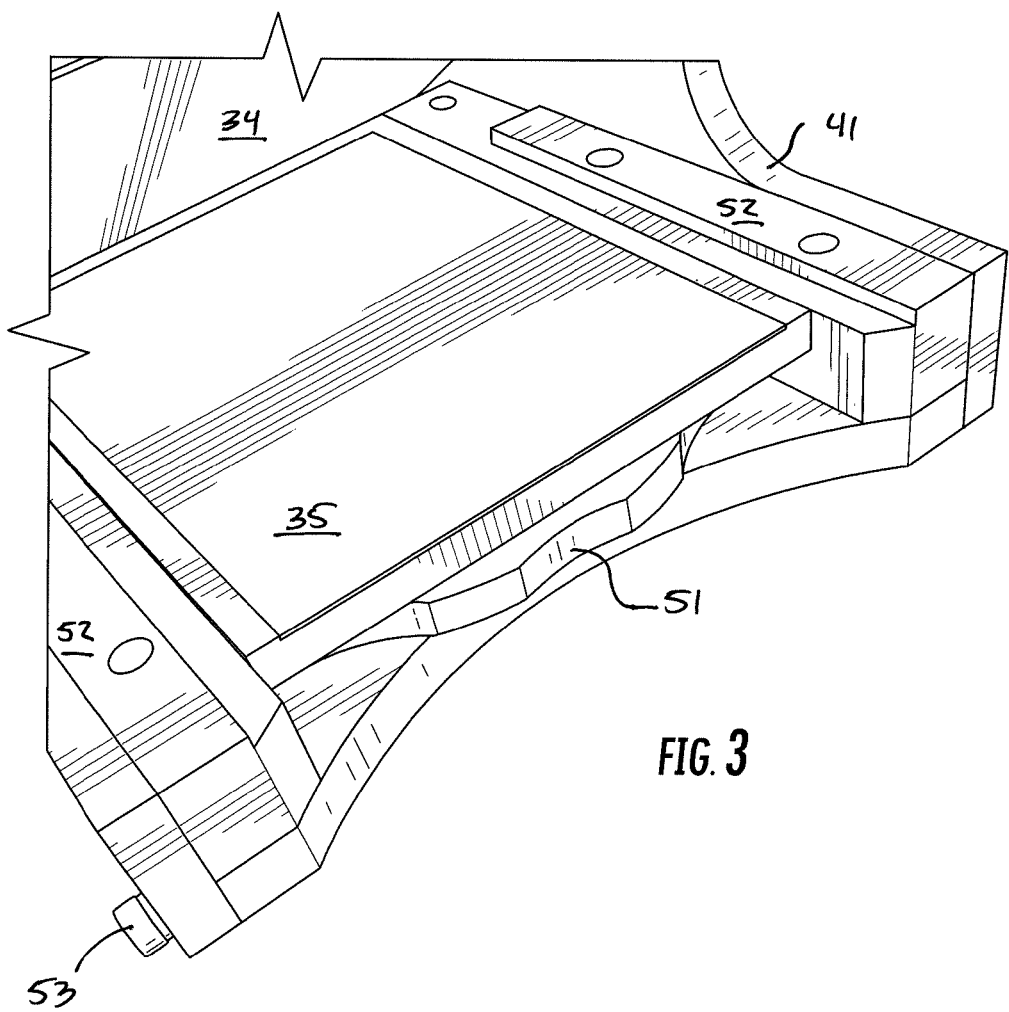
FIG. 3 is an enlarged partial perspective view of the lower press plate 35 and the plate adjustment dial 51 in position.
Figure 4:
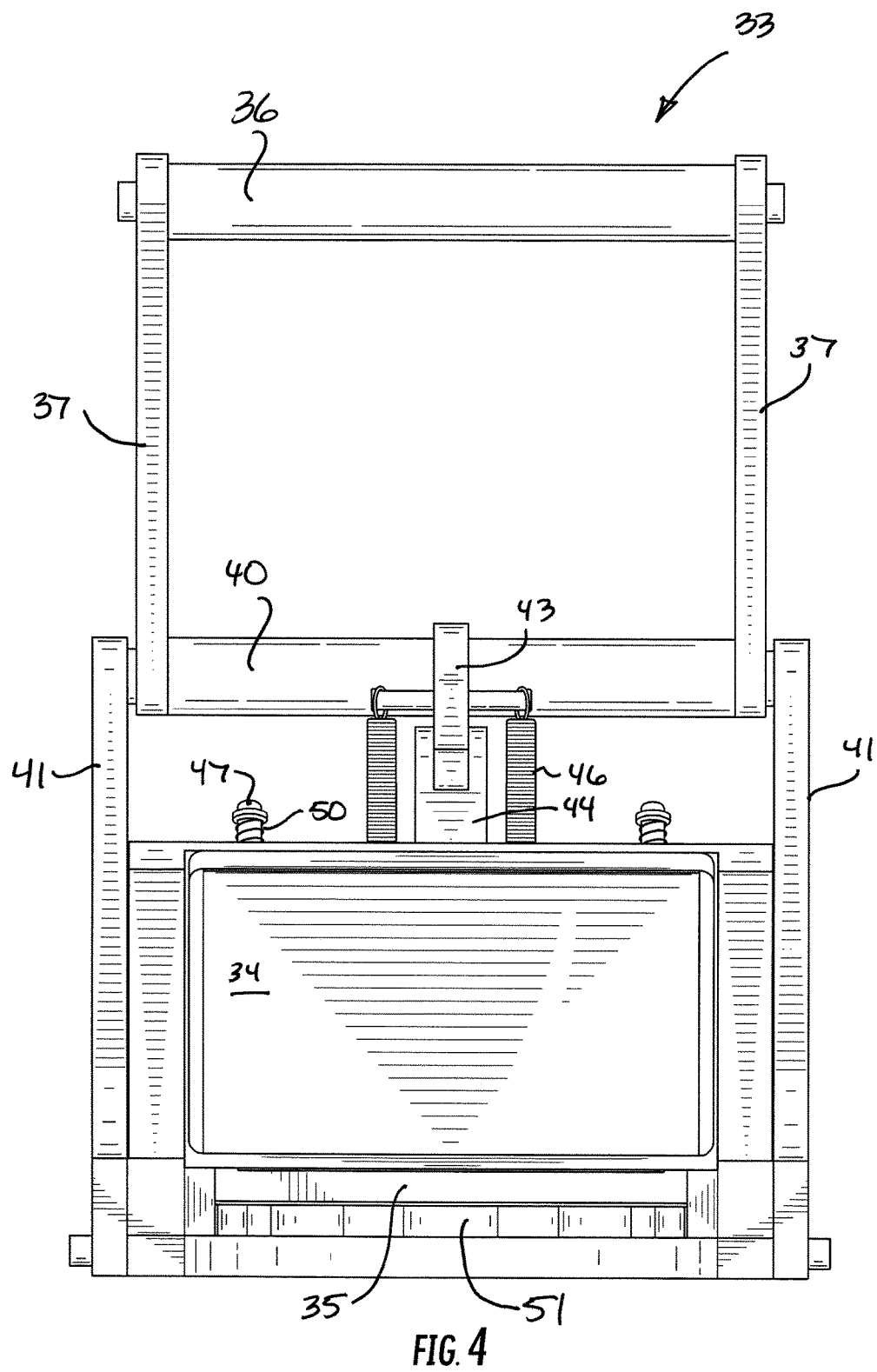
FIG. 4 is a front elevational view of the sample press 33 in the open position.
Figure 5:
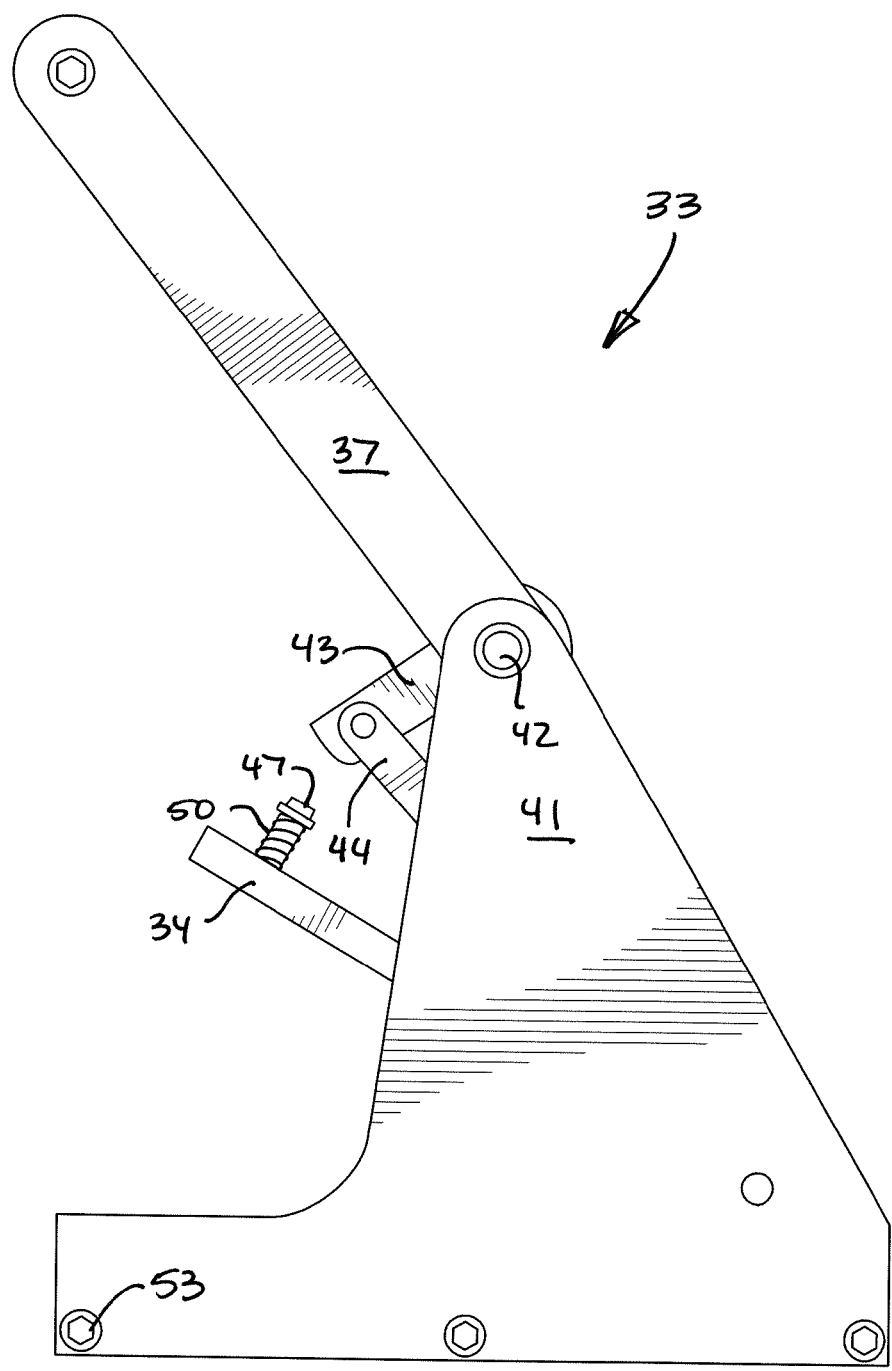
FIG. 5 is a side elevational view of the sample press 33 in the open position.
Figure 6:
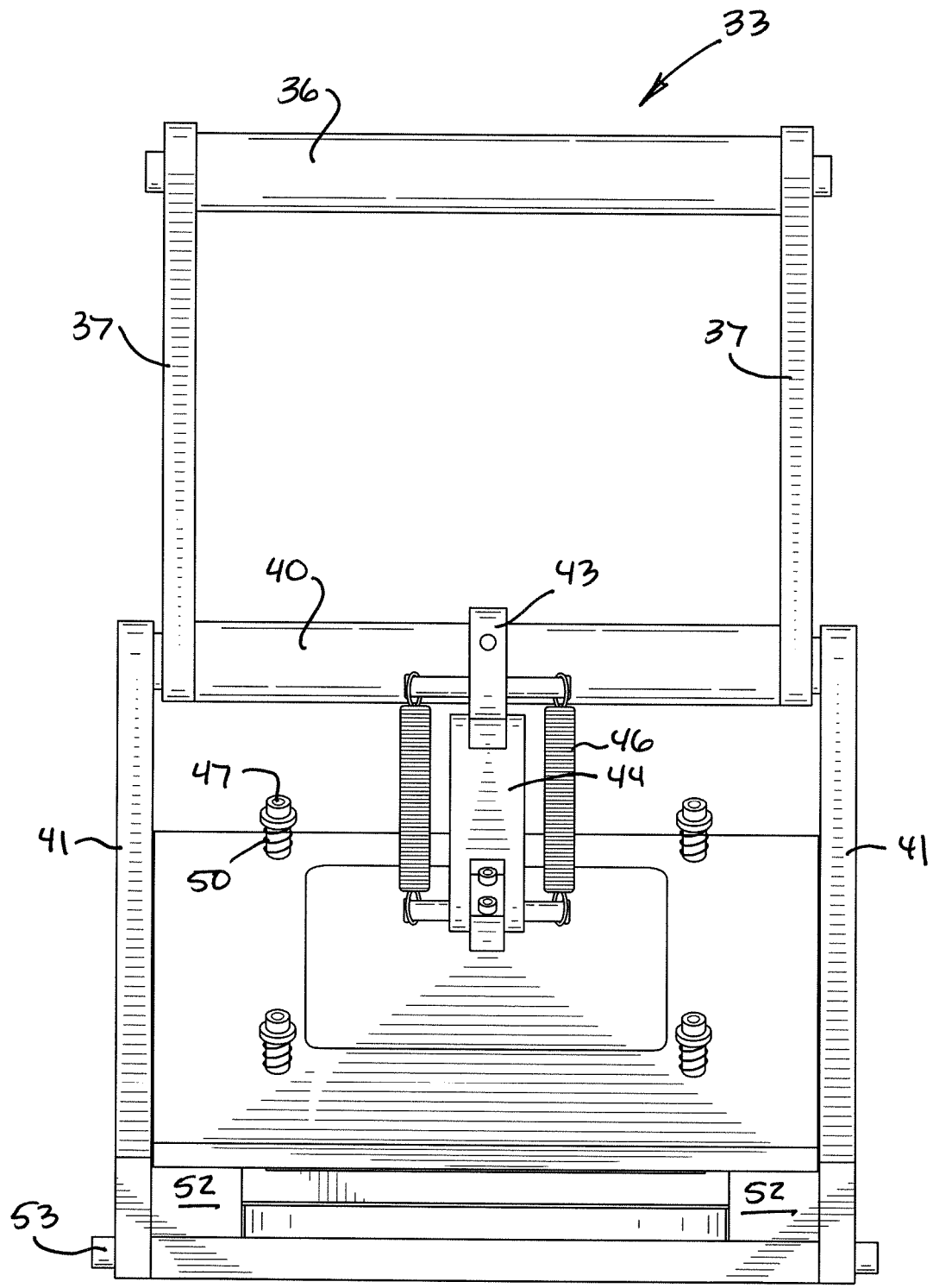
FIG. 6 is a rear elevational view of the sample press 33 in the open position.

FIG. 2 illustrates an exemplary sample press broadly designated at 33. The press helps prepare the sample in the manner described further herein with respect to the method.

Fundamentally, the press includes an upper press plate 34 and a lower press plate 35. A press handle 36 is connected to the upper press plate 34 through a pair of handle arms 37 and a press shaft 40, all of which are connected to a press frame (or yoke) 41 through a series of pins; e.g., shaft pin 42.

When the press handle 36 rotates the press shaft 40, the movement is transmitted through the crank arm 43 and the plate arm 44 to the upper press plate 34. The action is designed to press the sample into a substantially flat form 45 between respective sample pads 30 and 31.

Quartz pads of the necessary purity—i.e., free of the elements for which the test is being carried out—are not conventionally available. Conventional quartz pads must be pretreated to eliminate the relevant elements. As further qualifications, the pads are flexible, porous, absorbent, do not retain the ashed material when mixed with weak acid, and must not contain any binder (again, to eliminate the relevant elements).

A pair of arm springs 46 help provide mechanical advantage to the overall movement of the press, and a set of cushioning pins 47 and springs 50 permit a modest movement of the upper press plate 34 even in it's closed position.

The lower press plate 35 is connected to a plate adjustment dial 51 which is connected to a threaded riser (not shown) so that rotation of the plate adjustment dial 51 moderately raises or lowers the position of the lower press plate 35. This permits appropriate adjustment of the press with respect to different types of samples.

Other details of the sample press 33 include the plate frame members 52 and a series of fasteners 53, typically pins, rivets or bolts that secure the various parts of the press to one another.

The surfaces of the upper press plate 34 and lower press plate 35 can be conveniently formed of metal for strength and stability with a polymer coating (e.g., polyethylene, fluoropolymers) for ease-of-use and cleaning.

As set forth with respect to the method steps, following the ashing step, the ashed sample is placed into a container, illustrated as a typical beaker 63 holding a weak acid (e.g., dilute hydrochloric) in which the ashed sample will easily dissolve.

Because the flame photometer will essentially provide a concentration measurement, the volume of acid is either known or is specifically diluted to a known volume. The ashed sample and the pads (31 is illustrated) can be agitated easily with a device as simple as the stirring rod 65. As set forth elsewhere, the sample pads are free of any binders, and are manufactured by pressing the quartz fibers together. Accordingly, the sample pads 30 and 31 separate easily in the weak acid 64.

Figure 9:
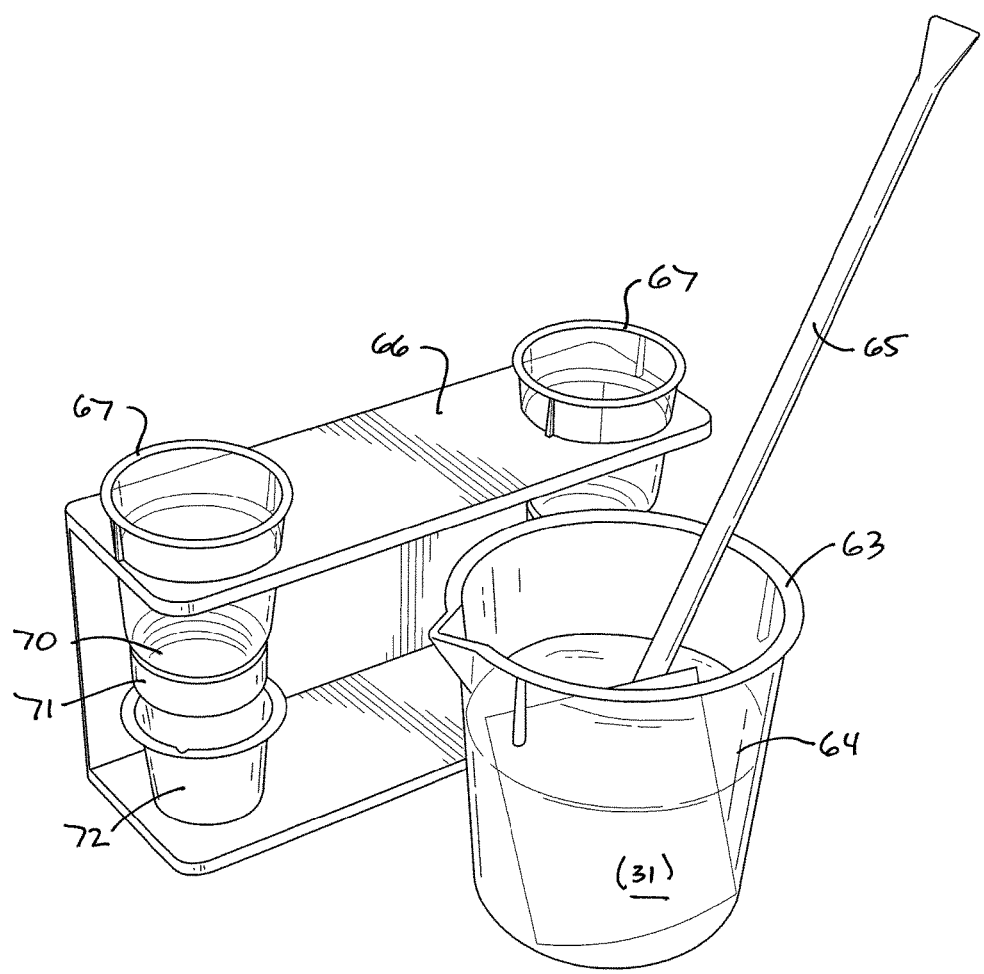
FIG. 9 is a perspective view of several of the items used to complete portions of the method.
Figure 10:
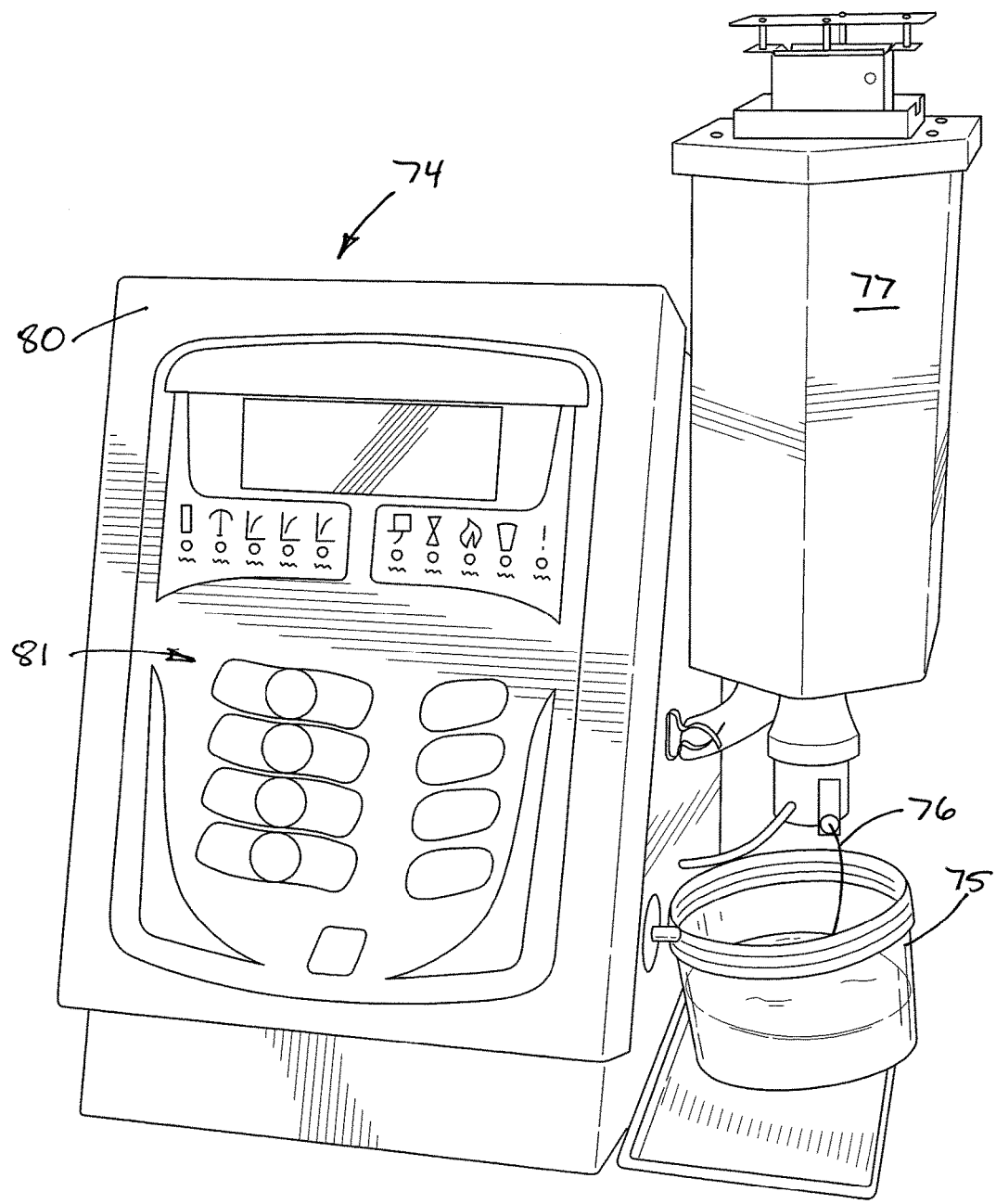
FIG. 10 is a perspective view of a flame photometer as used in the method of the invention.

FIG. 9 also illustrates that in a convenient arrangement, a filter rack 66 holds a pair of filter cups 67. The cup 67 carries a filter media 70 (paper, frit, etc.) which is supported in place by a perforated bottom portion 71 that allows the liquid filtrate to pass into the filtrate cup 72. As with the quartz pads, the filter media must be free of any of the elements for which the test is being carried out.

In summary, the ashed sample and pads are placed into the weak acid, the ashed sample is dissolved, and then the mixture of the ashed sample and the separated pads are filtered through the filter cup 67 into the filtrate cup 72. The filtrate in the cup 72 is thus prepared for the flame photometer.

Figure 8:
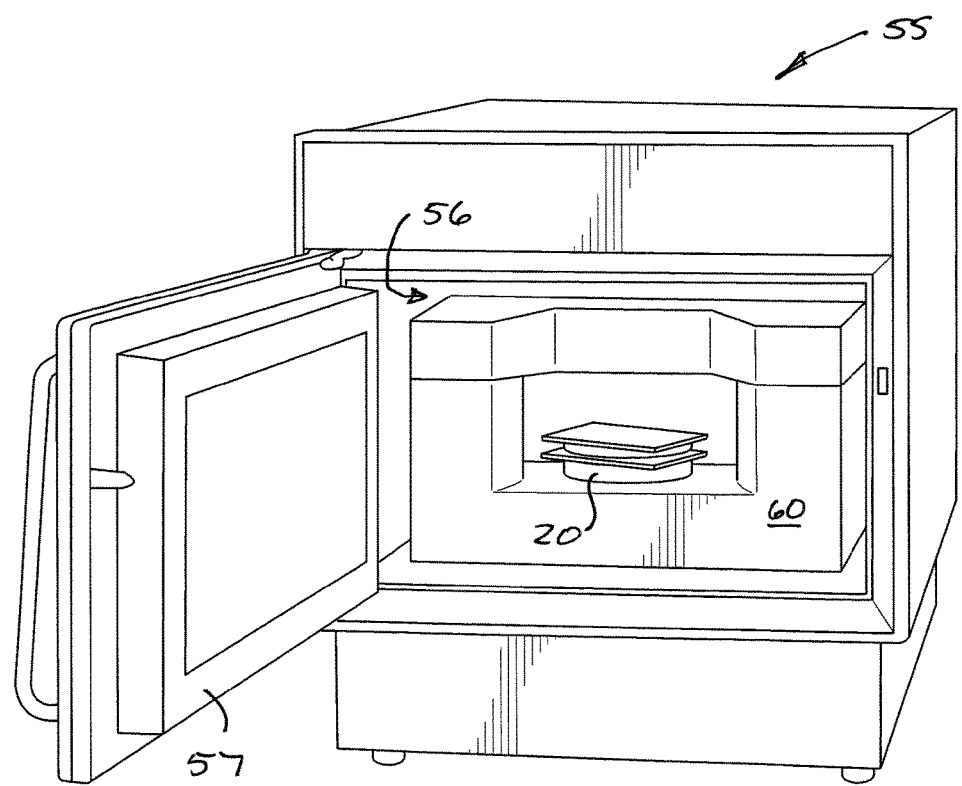
FIG. 8 is a perspective view of a sample in a microwave muffle furnace.

FIG. 8 is a perspective view of some of the equipment used in the method of the present invention. A furnace broadly designated at 55 defines a microwave cavity 56 in the general shape of a solid rectangle. As known to those familiar with the application of microwave radiation to materials and compositions, cavity designs that are more sophisticated than a solid rectangle are known and useful in many circumstances. For the purposes of the invention, however, the conventional rectangular solid cavity shape is generally sufficient.

It will be understood that a microwave furnace is used for speed and convenience, both of which are usually advantageous. The ashing step can, of course, be carried out using a more conventional oven, although the overall testing time is expected to be longer.

A door 57 defines the front wall of the microwave cavity 56 as well as a large portion of the front panel of the furnace 55. In some embodiments the furnace is referred to as a muffle furnace; a term used for a furnace in which the material undergoing heating is isolated to some greater or lesser extent from the fuel used to generate the heat and the resulting combustion products. In the microwave context, of course, no fuel needs to be isolated. Combustion products are generally removed by a fan (not shown) that exhausts the cavity.

Figure 7:
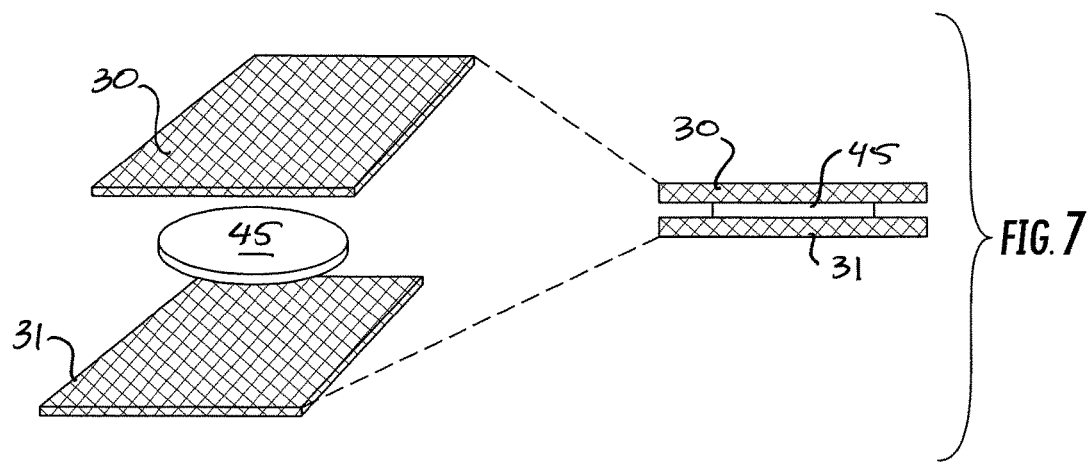
FIG. 7 is a combination cross-sectional and exploded perspective view of a sample according to the invention.

An appropriate refractory insulation material 60 is used to hold a prepared sample which in FIGS. 7 and 8 is broadly designated at 61. The refractory insulation can be any appropriate material which generally includes well-known conventional materials such as refractory brick (i.e. ceramics) or more recently developed refractory open cell foams. These materials are generally well understood in the art and will not be described in detail otherwise herein.

In the method of the invention, a sample, such as a sodium-containing food sample (of which cheese is a particularly helpful example) is weighed so that the proportion of the desired element can be eventually determined. The weighed sample is pressed between the sample pads 30 and 31. In particular, the sample is pressed to a thickness that under microwave radiation produces a steady-state temperature in the sample within no more than five minutes, in some cases no more than three minutes, and in some cases as rapidly as one minute or less.

FIG. 9 is a perspective view of the flame photometer broadly designated at 74. The detailed operation of flame photometers is generally well understood in the art and need not be explained or repeated here in detail. As a brief summary, a flame photometer includes a burner (and associated hardware) that can support and maintain a flame at a constant temperature and form; a mixing chamber or "nebulizer" which transports a homogeneous mixture of solution sample and gas to the flame at a steady rate; an optical color filter for isolating light of the wavelength/frequency corresponding to the emission of the element being measured; and a photodetector for measuring the intensity of the filtered radiation emitted from the flame.

In FIG. 9, a sample container is illustrated at 75 and a sample tube 76 connects the sample container 75 with the mixing chamber (not shown) in the housing 77.

In modern flame photometers, the output of the photodetector is amplified and transmitted using appropriate electronic circuitry maintained in the housing 80 which includes a control panel broadly designated at 81 and a display 82 for the output of the resulting measurement.

Without wishing to be bound by theory, the method comprises pressing the sample to a thickness that defines a small Biot number (in exemplary cases less than 1.0 and in some cases less than 0.1). As generally well understood in the heat transfer art, the Biot number gives an index of the ratio of the heat transfer inside of a body and at the surface of the body. Generally speaking, materials with very small Biot numbers (i.e., less than 1) demonstrate uniform temperature throughout the body; i.e., temperature gradients are negligible inside of the body.

The Biot number is defined as the product of the heat transfer coefficient of the material multiplied by its "characteristic length" and divided by the thermal conductivity of the material. The "characteristic length" is defined as the volume of the body divided by the surface area. As a result, the high surface area of the pressed sample of the invention helps minimize the Biot number.

In the ashing context, forming the sample into the pressed shape enables dry ashing to be carried out within the short time intervals just described in which microwave radiation is applied to the pressed sample and the pads 30 and 31 (i.e., the prepared sample 61) in the presence of a microwave susceptor material until the pressed sample ashes.

FIG. 8 illustrates the microwave susceptor material as a short cylinder 20 (the shape of the susceptor is generally not critical to the method) which can be selected from a number of microwave absorbing susceptor materials with silicon carbide (SiC) being widely available and easily adaptable to the present method. Other relevant susceptor materials can include titanium carbide, zirconium carbide, hafnium carbide, vanadium carbide, tantalum carbide, molybdenum carbide, niobium carbide, graphite, silicon boride, silicon nitride, zirconium boride, zirconium nitride, calcium boride and mixtures thereof.

As is well understood in the art, a susceptor material absorbs microwaves and converts the energy into heat more efficiently than many other materials, but without interfering with the operation of the microwave field in the cavity field in the destructive manner characteristic of a highly conductive metal.

In some cases, appropriate susceptors are combinations of ceramic binders and ceramic susceptor materials. In other cases, a susceptor can be a thin metal film on a microwave transparent substrate, a type of susceptor common in food preparation, but generally silicon carbide is quite convenient in the method of the invention.

The prepared sample 14 is then ashed in the furnace under the application of the microwaves until the pressed sample ashes. Because many spectrometry techniques use solution samples, the pads and the ashed sample is then added to an acid, and the filtrate from the pad-sample-acid mixture is forwarded to a spectrometer to determine the elements present and their amounts. Again, determination of the sodium content is exemplary.

Using the invention, it has been determined that the sample can be ashed within five minutes, or in as little as three minutes, or in some cases one minute or less. As those generally familiar with ashing techniques recognize, an appropriate temperature for ashing a food product is generally about 500° C. As an advantage of the present invention, ashing temperatures that approach 550° C. are quite sufficient. As set forth earlier, a number of elements begin to volatilize as temperatures approach or exceed 500° C. and in a testing protocol that seeks to capture an element, such a volatile loss produces inaccurate results.

The pads used in the invention are porous and hydrophilic (so that they can absorb portions of the pressed samples and in particular food products), have a low thermal mass that avoids interfering with or absorbing heat that is intended to ash the sample, are microwave transparent, have a high decomposition temperature that is unaffected by the method, and do not contain the element (e.g., sodium) being tested. Because the pads avoid the element being tested—typically sodium—they can be added to the acid along with the food sample without detrimentally affecting the test results. As used herein, an "absorbent" pad is generally hydrophilic and in particular will absorb water and oils common in food products.

Ashing is fundamentally a thorough oxidation of all of the materials in a sample other than minerals. The porous nature of the quartz pads is thus more helpful in these circumstances than the ceramic or specialized alloy crucibles used in other ashing tests. Additionally, because the pads can be added directly to the acid with the ashed sample, no transfer step (i.e., from crucible to acid) is required. Again, this adds to the speed of the test and reduces the experimental uncertainty.

Additionally, if the pads are of a known, precise weight—i.e., every pad is identical within the necessary uncertainties—the weighing step can follow the pressing step.

Prior to the evaluation in the spectrometer, the pads and the samples are added to a dilute acid selected from the group consisting of nitric ($HNO_3$), sulfuric ($H_2SO_4$), hydrochloric (HCl), and phosphoric ($H_3PO_4$) acids, and mixtures thereof. As set forth in the experimental sections, hydrochloric is most commonly used because it is widely available, inexpensive, and performs properly.

The sample is diluted to reach an appropriate content range from which the spectrometer, and in particular a flame photometer, will provide the most accurate and precise results. Generally a range of about 10 ppm-40 ppm is optimum for a flame photometer, but sodium can be measured over a range of 0-100 ppm. Other elements can be measured at similar (even if not identical) concentration ranges.

The flame photometer measures the concentration of the element (sodium) in the solution formed from the ashed sample, and thus the volume used for the dilution needs to be recorded. With the amount of solution being known, the parts per million in the flame can be multiplied by the volume of solution to provide the total sodium in the sample. The amount of sodium in the sample can then be expressed as a percentage simply by dividing the sample sodium by the initial sample weight.

A flame photometer conducts a controlled flame test in which the intensity of the flame color is representative of the associated element and its amount. Filters can be incorporated to limit the detection of colors and thus include (or exclude) elements of interest. In this regard, the characteristic emissions of sodium (589 nm), potassium (766 nm), lithium (670 nm), barium (554 nm) and calcium (622 nm) are readily distinguishable. Flame photometers are calibrated using standard solutions of the elements being tested. Although flame photometry is procedurally simple compared with some other techniques, its low cost and high suitability for determining Group 1 and Group 2 metals—sodium, potassium, lithium, barium, calcium—make it quite useful in the present method.

In another embodiment of the method, converting the sample to a sulfate salt (or combination of sulfate salts) can permit ashing temperatures as high as 900° C., and a sulfating step can be incorporated into the method of the invention. Experimental work confirms that although the results are precise, the accuracy is always about 5-10% . . . different from a test standard. This would appear to represent loss of volatile (i.e., unsulfated) material at these high temperatures. Nevertheless, the results are reproducible and thus useful. Sulfuric acid is harder to handle than dilute hydrochloric, of course, and arrangements for obtaining and working with a 900° C. furnace likewise add complexities.

Accordingly, the sulfate step is an option for the invention in certain circumstances if these points are understood.

As another advantage, it has been determined that the ashing step only needs to proceed until the salts in the resulting ash are fully soluble in a weak acid (e.g., 1-10%; 0.1-1.0M). Thus, although a full ashing will produce a white composition and is entirely appropriate for the invention, some leftover charred carbon that produces a gray ash does not adversely affect the results. As a result, the ashing step of the method can be somewhat shorter than a full ashing step (e.g., as carried out for "total ash content"), can save testing time and can thus add to the flexibility and usefulness of the invention.

78.2 Although the test is described herein in terms of a single sample, nothing about the method requires individual sample ashing. Thus, several samples can be ashed at the same time (either using microwave or conventional heating) provided that the ashed samples are thereafter segregated for dilution and flame photometry.

The microwave furnace is advantageous for the invention because all of it cycles are faster than conventional heating, no special tools are required and, because microwave should not rely on conduction or convection heating, The time required for long heating and cooling cycles can be totally eliminated.

Flame photometry is a particularly flexible test which allows a wide range of dilution while still providing accurate answers. Accordingly although a 200:1 dilution is frequently used in the invention, other dilution ranges can be incorporated as well for different purposes.

The filter paper (or other filtration media) used in the filtration step must likewise be free of the relevant elements. In some cases, filter paper of "analytical grade" for certain purposes or standards actually contain the relevant elements and thus a more precise material is required.

In another aspect, the invention is the sample itself which represents a pressed layer of a food product between two layers of a material that is porous, has low thermal mass, is microwave transparent, has high decomposition temperature, and does not contain the element being tested.

In a typical embodiment used for sodium content testing, the sample is a pressed layer of cheese between two quartz fiber pads.

Experimental

The method of the invention was carried out using a flame photometer from BWB Technologies USA (www.bwbtech.com). The flame photometer was otherwise conventional and required no modification to be used in the method.

Following the ashing step, in several experiments 5 ml of a 25% hydrochloric acid solution was used to wet the ash, and then diluted to 100 mL Alternatively, 100 ml of a 1% hydrochloric acid solution mixed with the ash sample gave the same results. Deionized water did not produce appropriate recoveries.

Sulfuric acid ($H_2SO_4$) can theoretically withstand ashing temperatures higher than can hydrochloric acid, and was tested in the method, but did not provide (in these tests) any observed advantages.

As an optional step, some of the organic material can be removed by treating the sample with magnesium nitrate or nitric acid prior to the ashing step.

Prior Art Example

A comparison was carried out by using a current wet digestion technique to prepare a sample followed by ICP for quantitative analysis. Table 1 describes some of the conditions.

Analytes: Na (Sodium)

Reagents: Nitric acid (conc.)

Procedure: Weigh 0.25 g of cheese into a microwave transparent vessel and add 10 ml of Nitric acid to each vessel. Apply microwave radiation at a power level and for a time sufficient to digest the sample. After cooling, transfer each digested solution to a 100 ml Teflon volumetric flask and dilute to volume with deionized water.

TABLE 1

| Conditions During Digestion of Cheese | | | |
|---|---|---|---|
| Temperature at End of Ramp (° C.) | 210 | Pressure at End of Ramp (psi) | N/A |
| Temperature at End of Hold (° C.) | 210 | Pressure at End of Hold (psi) | N/A |

While preparing the microwave transparent vessels two nitric acid cleans are completed on the vessels. When transferring the sample to the vessel a clean spatula is used and cleaned with deionized water between every sample transfer. After the sample is placed into the liner, the lid is added immediately after adding the acid. Because sodium contamination can be found in many places, each sample must be treated delicately.

Comparison

Table 2 compares samples analyzed for Na by ICP to those analyzed by flame photometer. The ICP samples were first prepared by doing an acid digestion, whereas the flame photometer results used the 4 minute dry ashing procedure according to the present invention.

TABLE 2

| Sodium Analysis | | |
|---|---|---|
| Sample Type | ICP Method mg/100 g | Flame Photometry Method mg/100 g |
| Cheese slice | 680 | 689 |
| Cheese slice | 868 | 884 |
| Cheese slice | 1015 | 1022 |
| Cheese slice | 1190 | 1221 |
| Cheese slice | 1350 | 1352 |
| Cheese slice | 1470 | 1478 |
| Mild Cheddar | 770 | 765 |
| Cream Cheese | 344 | 344 |
| Cream Cheese with chives and onion | 373 | 370 |

Table 3 shows the accuracy and precision of the Dry Ash/Flame Photometer Na method.

TABLE 3

| Sample No. | Initial Weight (g) | ppm | mg Na/100 g |
|---|---|---|---|
| 1 | 0.2594 | 13.5 | 1041 |
| 2 | 0.2520 | 12.9 | 1024 |
| 3 | 0.2569 | 13.1 | 1020 |
| 4 | 0.2498 | 12.7 | 1017 |
| 5 | 0.2561 | 13.0 | 1015 |
| 6 | 0.2569 | 13.1 | 1020 |
| 7 | 0.2546 | 13.0 | 1021 |
| 8 | 0.2568 | 13.1 | 1020 |
| Results | | | |
| 1022 | | Mean | |
| 8.0311 | | STD | |
| 0.79% | | RSD | |
| 26 | | Range | |

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of preparing a food sample for quantitative element testing comprising:

pressing a weighed solid sample that defines a Biot number greater than 1.0 into a substantially flat form between pads that are microwave transparent, porous, have low thermal mass, have high decomposition temperatures, and do not contain elements selected from the group consisting of sodium, potassium, barium, lithium, and calcium, to a thickness that defines a Biot number less than 1.0; and applying microwave radiation to the pressed sample and pads in the presence of a microwave susceptor material to ash the pressed sample until the ash will release the salts in the food sample into a weak acid.

2. A food sample preparation method according to claim 1 further comprising adding the pads and the ashed sample to a dilute acid; filtering the mixture of sample, pads and acid; and forwarding filtrate from the pad-sample-acid mixture to a flame photometer.

3. A food sample preparation method according to claim 1 comprising applying the microwave radiation in the presence of the susceptor until the pressed sample reaches a temperature greater than 500° C. but not exceeding 550° C.

4. A food sample preparation method according to claim 1 wherein the step of pressing the weighed sample between pads comprises pressing the weighed sample between quartz fiber pads.

5. A method of element testing comprising:

weighing a solid sample that defines a Biot number greater than 1.0;

pressing the weighed solid sample into a substantially flat form between pads that are microwave transparent, porous, have low thermal mass, have high decomposition temperatures, and do not contain elements selected from the group consisting of sodium, potassium, barium, lithium, and calcium to a thickness that defines a Biot number less than 1.0 and that under microwave radiation produces a steady-state temperature in the sample within five minutes;

applying microwave radiation to the pressed sample and pads in the presence of a microwave susceptor material to ash the pressed sample until the ash will release the salts in the food sample into a weak acid;

adding the pads and the ashed sample to an acid; and forwarding filtrate from the pad-sample-acid mixture to a spectrometer.

6. A method of element testing according to claim 5 comprising forwarding the filtrate to a spectrometer that operates a method selected from the group consisting of flame photometry, inductively coupled plasma atomic emission, inductively coupled plasma mass spectroscopy, and atomic absorption spectroscopy.

7. A method of element testing according to claim 5 comprising pressing the sample to a thickness that under microwave radiation produces a steady-state temperature in the sample within one minute.

8. A method of element testing according to claim 5 comprising applying microwave power to the sample and pads in the presence of a susceptor selected from the group consisting of thin metal films, silicon carbide, titanium carbide, zirconium carbide, hafnium carbide, vanadium carbide, tantalum carbide, molybdenum carbide, niobium carbide, graphite, silicon boride, silicon nitride, zirconium boride, zirconium nitride, calcium boride and combinations of ceramic binders and ceramic susceptor materials.

9. A method of element testing according to claim 5 comprising applying microwave radiation until the pressed sample reaches an ashing temperature that does not exceed 550° C.

10. A method of element testing according to claim 5 comprising adding the pads and the ashed sample to a dilute acid selected from the group consisting of nitric, sulfuric, hydrochloric and phosphoric acids and mixtures thereof.

* * * * *